United States Patent [19]

Rollmann

[11] 4,300,011

[45] Nov. 10, 1981

[54] SELECTIVE PRODUCTION OF AROMATICS

[75] Inventor: Louis D. Rollmann, Princeton, N.J.

[73] Assignee: Mobil Oil Corporation, New York, N.Y.

[21] Appl. No.: 144,740

[22] Filed: Apr. 28, 1980

[51] Int. Cl.³ .......................... C07C 2/68; C07C 5/22
[52] U.S. Cl. .................................. 585/467; 585/470; 585/475; 585/481; 585/733
[58] Field of Search ............... 585/467, 470, 475, 481

[56] References Cited

U.S. PATENT DOCUMENTS 4,158,676 6/1979 Smith et al. ...................... 585/481

*Primary Examiner*—Curtis R. Davis

*Attorney, Agent, or Firm*—Charles A. Huggett; Michael G. Gilman; Dennis P. Santini

[57] ABSTRACT

Selective reactions of hydrocarbons and/or oxygenated hydrocarbons are conducted in the presence of catalysts comprising one or more zeolites characterized by a silica to alumina mole ratio of at least 12 and a constraint index in the approximate range of 1 to 12, said catalysts are contacted with bulky heterocyclic organic nitrogen compounds. Said nitrogen compounds have an effective critical dimension of greater than 6.2 Angstroms and a pKa of between about 3 and 9. The process of this invention is particularly useful in the production of dialkylbenzene derivatives low in the ortho-isomer.

36 Claims, No Drawings

SELECTIVE PRODUCTION OF AROMATICS

BACKGROUND OF THE INVENTION

1. Field of the Invention

This invention relates to the conducting of selective reactions for the production of aromatics. More particularly, the present invention concerns carrying out such reaction by the utilization of a catalyst comprising a novel class of zeolites in contact with large heterocyclic nitrogen containing organic compounds.

2. Description of the Prior Art

The novel class of zeolites characterized by a silica to alumina mole ratio of at least 12 and a constraint index in the approximate range of 1 to 12 has been found to be extremely useful as an active catalyst component in conducting various selective and shape-selective reactions. This class of zeolites shall hereinafter be referred to as "ZSM-5 class zeolites" and shall mean to include ZSM-5 zeolite and/or other zeolites in the class, e.g., ZSM-11, ZSM-12, ZSM-23, ZSM-35, ZSM-38, etc.

Selective reactions catalyzed by ZSM-5 class zeolites include the alkylation of aromatics, e.g., selective production of para dialkyl substituted benzenes, selective ethylation of benzene and mono alkyl benzenes, and the selective production of para-xylene by the methylation of toluene; disproportionation of toluene (2 Toluene→Benzene+Xylene); xylene isomerization; and alcohol/ether conversion to hydrocarbons; e.g. methanol to gasoline range product, just to name a few.

U.S. Pat. Nos. 3,751,504 and 3,751,506 and literature articles such as J. Catalysis, 61, 477 (1980) generally describe vapor phase alkylation of aromatic hydrocarbons with olefins, e.g., benzene with ethylene, in the presence of a ZSM-5 class zeolite catalyst.

The selective production of alkyl substituted benzene compounds including para dialkyl substituted benzenes and selective ethylation of mono alkyl benzenes over ZSM-5 class zeolites is generally described in the following U.S. Pat. Nos. 4,086,287; 4,094,921; 4,100,217; 4,104,319; 4,117,024; 4,117,026; 4,127,616; 4,128,592; 4,143,084; and 4,136,128.

The selective production of para-xylene by the methylation of toluene in the presence of ZSM-5 class zeolites is given in such U.S. Pat. Nos. as 3,965,207; 4,049,738; 4,080,395; and 4,080,396 and in J. Amer. Chem. Soc., 101, 6783 (1979). Modification of ZSM-5 class zeolites for this reaction utilizing metal and metal oxides, e.g., boron, antimony oxide, magnesium and phosphate compounds, is disclosed in the following U.S. Pat. Nos. 4,029,716 (boron); 4,067,920 (boron); 4,078,009 (boron); 4,067,919 (antimony oxide); 4,113,788 (magnesium); 4,158,024 (magnesium); 4,034,053 (magnesium); and 4,152,364 (phosphate compound). Pretreatment of ZSM-5 class zeolites for the selective production of p-xylene is described in U.S. Pat. No. 3,965,209 (steam treatment); U.S. Pat. No. 3,965,210 (surface of catalyst modified by contact with a polymer made-up of metacarbonate units connected by siloxane units); and U.S. Pat. No. 4,001,346 (precoking).

Disproportionation of toluene over ZSM-5 class zeolites is generally described in the following U.S. Pat. Nos. 4,011,276; 4,016,219; 4,052,476; 4,097,543; 4,098,837; 4,160,788; and 4,182,923. Many of these toluene disproportionation patents disclose the use of metal, e.g. phosphorous and magnesium, with the ZSM-5 class zeolite.

The utilization of ZSM-5 class zeolites for xylene isomerization is described in the following U.S. Pat. Nos. 3,856,871; 3,856,873; 4,101,596; 4,152,363 and 4,163,028.

The conversion of alcohols and/or ethers to valuable hydrocarbons, e.g., olefins and/or gasoline range material, in the presence of ZSM-5 class zeolites is generally disclosed in the following U.S. Pat. Nos. 3,894,103; 3,894,106; 3,894,107; 3,899,544; 3,928,483; 3,998,899; 4,083,888; and 4,083,889. Disclosure of this nature is also found in numerous scientific publications such as J. Catalysis 47, 249 (1977); J. Catalysis 53, 40 (1978); and J. Catalysis 61, 155 (1980).

In many of these aforementioned patents, substances such as P, Mg, $SiO_2$ and C are used to poison binder activity and to increase diffusion constraints. It is one object of this invention to produce useful materials such as vinyl toluenes without resorting to the use of such substances. It is another object of this invention to provide a useful technique for further improving the selectivity of zeolite catalysts which do contain such substances as P. Mg, $SiO_2$, C, etc. It is yet another object of this invention to provide a novel process for conducting selective reactions for the production of aromatics.

SUMMARY OF THE INVENTION

In accordance with the instant invention, there has now been discovered a novel process for conducting selective reactions of hydrocarbons and/or oxygenated hydrocarbons. The process involves the contacting of such hydrocarbons in the presence of one or more zeolites characterized by a silica to alumina mole ratio of at least 12 and a constraint index in the approximate range of 1 to 12 (a ZSM-5 class zeolite), which is contacted either intermittently or continuously, with one or more bulky heterocyclic organic nitrogen compounds having a pKa of between about 3 and 9. The size of said nitrogen compounds are such that they possess an effective critical dimension, for purposes of entrance into the zeolite pore structure, exceeding that for pyridine, i.e. of greater than 6.2 Angstroms. The process of this invention is particularly advantageous in the production of dialkylbenzene derivatives low in the ortho-isomer.

Selective reactions that would be applicable to this invention include alkylation of aromatics, toluene disproportionation, xylene isomerization, and alcohol/ether conversion to valuable hydrocarbons.

DESCRIPTION OF THE PREFERRED EMBODIMENTS

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having much higher silica to alumina mole ratios, i.e. up to 16,000 or higher.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. (1000° F.) for at least 15 minutes. The zeolite is then flushed with helium and the temperature is adjusted between 290° C. (550° F.) and 510° C. (950° F.) to give an overall conversion of between 10% and 60%. The mixture of hydrocarbons is passed at 1 liquid hourly space velocity, i.e., 1 volume of liquid hydrocarbon per volume of zeolite per hour, over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. (1000° F.) and a liquid hourly space velocity of less than one, such as 0.1 or less, can be employed in order to achieve a minimum total conversion of about 10%.

There also may be instances where the activity is so low, e.g., high silica to alumina mole ratio, that the Constraint Index cannot be adequately measured, if at all. In such situations, Constraint Index is meant to mean the Constraint Index of the exact same substance, i.e. same crystal structure as determined by such means as X-ray diffraction pattern, but in a measurable form, e.g., high aluminum containing form.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (C.I.) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (Mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence of absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g., 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. No. 3,702,886 and U.S. Pat. No. Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire contents thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

The composition ZSM-48 can be identified, in terms of moles of anhydrous oxides per 100 moles of silica, as follows:

(0 to 15)RN: (0 to 1.5)$M_{2/n}$O: (0 to 2)$Al_2O_3$: (100) $SiO_2$ wherein M is at least one cation having a valence in, RN is a $C_1$-$C_{20}$ organic compound having at least one amine functional group of pKa $\geq$ 7, and wherein the composition is characterized by the distinctive X-ray diffraction pattern as shown in Table 1 below.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN + H_2O$.

The X-ray diffraction pattern of the ZSM-48 has the following significant lines:

TABLE 1

| CHARACTERISTIC LINES OF ZSM-48 | |
|---|---|
| d | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart.

From these, the relative intensities, 100 $I/I_o$, where $I_o$ is the intensity of the strongest line or peak, and d (obs.), the interplanar spacing in A, corresponding to the recorded lines, were calculated. In Table 1 the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum mole ratio of the particular sample, as well as if it has been subjected to thermal treatment.

ZSM-48 can be prepared from a reaction mixture containing a source of silica, RN, and alkali metal oxide, e.g. sodium, water, and optionally alumina, and having a composition, in terms of mole ratios of oxides, falling within the following ranges:

| REACTANTS | BROAD | PREFERRED |
|---|---|---|
| $Al_2O_3/SiO_2$ | = 0 to 0.02 | 0 to 0.01 |
| $Na/SiO_2$ | = 0 to 2 | 0.1 to 1.0 |
| $RN/SiO_2$ | = 0.01 to 2.0 | 0.05 to 1.0 |
| $OH^-/SiO_2$ | = 0 to 0.25 | 0 to 0.1 |
| $H_2O/SiO_2$ | = 10 to 100 | 20 to 70 |
| $H+$(added)/$SiO_2$ | = 0 to 0.2 | 0 to 0.05 | wherein RN is a $C_1$-$C_{20}$ organic compound having amine functional group of pKa$\geq$7, and maintaining the mixture at 80°-250° C. (175° F.-480° F.) until crystals of ZSM-48 are formed. H+(added) is moles acid added in excess of the moles of hydroxide added. In calculating H+(added) and OH values, the term acid (H+) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48, no alumina is added. The only aluminum present occurs as an impurity.

Preferably, crystallization is carried out under pressure in an autoclave or static bomb reactor, at 80° C. (175° F.) to 250° C. (480° F.). Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of pKa $\geq 7$ and includes such compounds as $C_3$–$C_{18}$ primary, secondary, and tertiary amines, cyclic amine, such as piperidine, pyrrolidine and puperazine, and polyamines such as $NH_2$—$C_nH_{2n}$—$NH_2$ wherein n is 4–12.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such zeolites wherein the mole ratio of silica to alumina could be very high. The incorporation of the identified patents should therefore not be construed as limiting the disclosed crystalline zeolites to those having the specific silica to alumina mole ratios discussed therein. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. (1000° F.) for one hour, for example, followed by base exchange with ammonium salts followed by calcination at 540° C. (1000° F.) in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. (1000° F.) for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 100 lbs. per cubic foot (1.6 grams per cubic centimeter). It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article ZEOLITE STRUCTURE by W. M. Meier. This paper, the entire contents of which are incorporated herein by reference, is included in PROCEEDINGS OF THE CONFERENCE ON MOLECULAR SIEVES (London, Apr., 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume cc/cc | Framework Density g/cc |
| --- | --- | --- |
| Ferrierite | 0.28 | 1.76 |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used.

As is the case of many catalysts, it is desired to incorporate the zeolite with another material resistant to the temperatures and other conditions employed in organic conversion processes. Such materials include active and inactive materials as well as inorganic materials such as clays, silica and/or metal oxides. Inactive materials suitably serve as diluents to control the amount of conversion in a given process so that products can be obtained economically and orderly without employing other means for controlling the rate of reaction.

Binders useful for compositing with the useful zeolite herein also include inorganic oxides, notably alumina, which is particularly preferred.

In addition to the foregoing materials, the zeolite catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The relative proportions of finely divided crystalline zeolite and inorganic oxide matrix vary widely with the zeolite content ranging from about 1 to about 90 percent by weight and more usually in the range of about 2 to about 65 percent by weight of the composite.

The above described zeolites contact, either intermittently or continuously, a bulky heterocyclic organic nitrogen compound having an effective critical dimension for entrance into the zeolite pore structure exceeding that of pyridine, i.e. of greater than 6.2 Angstroms.

The concept of an "effective critical dimension" of a molecule is described by Breck on pages 633 to 641 in *Zeolite Molecular Sieves*, John Wiley & Sons, Inc. (1974), the entire contents of which are incorporated herein by reference. Generally, this dimension is the smallest dimension that will permit passage through the pores of the zeolite, i.e., the dimension that most nearly approaches the pore size of the zeolite. For example, the critical dimension of n-hexane is the thickness not the length, while the critical dimension for benzene is the cross-sectional diameter, rather than the thickness.

Bulky heterocyclic organic nitrogen compounds useful in this invention are heterocycles containing aryl and alkyl substituents with the preferred substituents being methyl and phenyl groups. Specific non-limiting examples of such heterocycles include alkylated pyridine derivatives such as collidine (2,4,6-trimethylpyridine), 3,4-lutidine (3,4-dimethylpyridine) and pentamethylpyridine; quinoline and alkylated quinolines such as 4-methylquinoline, 2,4- and 4,8-dimethylquinolines, and 2,4,8-trimethylquinoline; and three-ring heterocycles such benzoquinolines, e.g., 5,6- and 7,8-benzoquinolines, and phenanthrolines, e.g., 1,10-phenanthroline, and their derivatives such as neocuproine (2,9-dimethyl-1,10-phenanthroline) and bathophthenanthroline (4,7-diphenyl-1,10-phenanthroline). One will note that all of the above described examples consist of structures containing the pyridine moiety, either alone, fused, or linked with up to four other aromatic rings. The above described heterocycles may also have substituent groups such as halogens, hydroxyl groups, etc. associated therewith.

Effective critical dimensions for the purposes of this invention were determined by the use of CPK (Corey-Pauling-Koltun) space-filling atomic models, obtained from Ealing Corporation, Natick, Mass. The following Table illustrates critical dimensions measured from such models with corresponding pKa values for several heterocyclic compounds.

| | Effective Critical Dimension, Angstroms | pKa |
|---|---|---|
| Pyridine | 6.2 | 5.2 |
| 2,6-Lutidine | 6.6 | 6.8 |
| 3,4-Lutidine | 7.0 | 6.5 |

-continued

| | Effective Critical Dimension, Angstroms | pKa |
|---|---|---|
| 4-Methylquinoline | 7.3 | 5.2 |
| 4,8-Dimethylquinoline | 7.4 | N.A. |
| 2,4,6-Collidine | 7.5 | 7.4 |
| 5,6-Benzoquinoline | 7.5 | 5.2 |
| 7,8-Benzoquinoline | 7.5 | 4.2 |
| 1,10-Phenanthroline | 7.5 | 4.8 |
| 2,4-Dimethylquinoline | 7.5 | 5.1 |
| Pentamethylpyridine | 7.7 | N.A. |
| 2,4,8-Trimethylquinoline | 7.9 | 4.5 |
| Neocuproine | 8.3 | N.A. |
| Bathophenanthroline | 9.5 | N.A. | pKa values for the above Table were taken from *Physical Methods in Heterocyclic Chemistry*, A. R. Katritzky, Academic Press, Vol. I, 1963, Chapter 1 by A. Albert.

In aromatics production in accordance with this invention, the desired effect of improving selectivity can only be achieved by the use of heterocycles larger than pyridine, since pyridine is a catalyst poison. Thus the larger heterocycles are preferred, those of dimension larger than about 6.8 Angstroms, and preferably larger than 7.0 Angstroms. As will be seen later in the examples, however, solubility, vapor pressure and sheer size become constraints for very large heterocycles, and compounds such as bathophenanthroline (9.5 Angstroms) are slightly less effective than compounds having an intermediate size.

Steaming may alter the susceptibility of a zeolite catalyst to a given heterocycle. To be effective, such steaming will preferably be accomplished prior to catalyst use by contacting the otherwise finished catalyst with steam at a pressure of between about 1.0 kPa (0.2 psia) and 245 kPa (35 psia), a temperature of between about 320° C. (610° F.) and greater than 650° C. (1200° F.), for a period of time (contact time) between about 30 minutes and 24 hours. Preferred steaming conditions include a pressure of between about 50 kPa (7 psia) and 150 kPa (22 psia), a temperature of between about 400° C. (750° F.) and 550° C. (1020° F.), and a contact time of between about 1 hour and 10 hours. Steaming may also occur, however, as part of a normal aspect of catalyst use, e.g., in regeneration cycles or in conversion of oxygenated hydrocarbons.

The amount of nitrogen compound required and the mode of its injection into the process can vary. The compound will generally be added to the reaction, either in a large intial slug, in a constant amount, or in some combination of the two. When nitrogen compounds are used which are neither destroyed or irreversibly deposited on the zeolite, such nitrogen compounds may be effective as heat transfer mediums, or solvents for the reaction. In such cases, when the nitrogen compound serves as a heat transfer medium or as a solvent it may represent as much as 10% to 90% of the total reaction feed. More commonly however, much smaller amounts of heterocycles are utilized.

When an initial slug of nitrogen compound is employed to quickly establish the requisite selectivity, the level of said compound in the feed would be determined by the space velocity and the time allotted for attaining that selectivity. An initial slug of nitrogen compound can contain as much as 100 ppm to 5000 ppm nitrogen to total feed.

The amount of nitrogen as nitrogen compound can generally very between about 5 ppm and 15% of the total feed and preferably between about 10 ppm and 5000 ppm nitrogen to total feed. It will be appreciated that at higher temperatures, greater amounts of nitrogen compounds will be required. The use of a smaller crystal size zeolite will result in a greater amount of nitrogen compound required.

Nitrogen compounds will differ in their individual effectiveness due to differing equilibria for retention on the catalyst. 5,6-benzoquinoline, for example, has the same size as 1,10-phenanthroline and it is a slightly stronger base than 1,10-phenanthroline, yet greater amounts of the benzoquinoline are required to obtain the same catalyst selectivity obtainable by use of the phenanthroline.

Without wishing to be bound by any particular theory of operability, it is believed that said bulky heterocyclic organic nitrogen compounds act as selective catalyst poisons. Utilization of these "selectively poisoned catalysts" is quite appropriate for producing dialkylbenzene derivatives which are low in the ortho isomer, e.g., in producing ethyltoluenes with reduced ortho-isomer formation and with para-isomer content ranging from between about 30% and 97% and above.

Alkylation of aromatics concerns the reaction of an aromatic compound and an alkylating agent. The alkylating agent is an olefin or an alcohol, e.g., an olefin precursor. Reactions covered by the broad definition of alkylation of aromatics and thus appropriate reactions for this invention include the selective production of predominantly para dialkyl substituted benzene compounds, the selective ethylation of benzene and of mono alkyl benzene compounds and the selective production of para-xylene by the methylation of toluene. The novel process of the instant invention is particularly useful in the production of dialkyl substituted benzene compounds which are very low in the ortho-isomer.

Conversion conditions for alkylation of aromatics include a temperature of between about 40° C. (105° F.) and 600° C. (1110° F.), preferably between about 200° C. (390° F.) and 450° C. (840° F.); a pressure of between about 100 kPa (0 psig) and 7,000 kPa (1000 psig), preferably between about 275 kPa (25 psig) and 3500 kPa (500 psig); a weight hourly space velocity (WHSV) of between about 0.1 and 200, preferably between about 1 and 50; and a mole ratio of alkylation agent to aromatic compound of between about 0.05 and 20, preferably between about 0.10 and 5.

When the disproportionation of toluene is practiced according to the present invention, conversion conditions include a temperature of between about 200° C. (390° F.) and 600° C. (1110° F.), preferably between about 430° C. (800° F.) and 550° C. (1020° F.); a pressure of between about 100 kPa (0 psig) and 7,000 kPa (1000 psig), preferably between about 275 kPa (25 psig) and 3500 kPa (500 psig); and a WHSV of between about 0.01 and 20, preferably between about 0.5 and 5.

Conversion conditions for conducting xylene isomerization in accordance with the present invention include a temperature of between about 260° C. (500° F.) and 540° C. (1000° F.) and preferably between about 320° C. (600° F.) and about 490° C. (900° F.); a pressure of between about 275 kPa (25 psig) and about 7000 kPa (1000 psig), preferably from between about 275 kPa (25 psig) and about 2860 kPa (400 psig); and a weight hourly space velocity of between about 1 and about 50 and preferably between about 5 and about 15. It is preferred to carry out xylene isomerization in accordance with this invention in the presence of hydrogen. If hydrogen is used, the hydrogen/hydrocarbon mole ratio is between about 1 and 20 and preferably between about 2 and 8.

When the selective reaction conducted according to this invention is the conversion of alcohols and/or ethers to valuable hydrocarbons, conversion conditions include a temperature of between about 260° C. (500° F.) and 540° C. (1000° F.), preferably between about 320° C. (600° F.) and 460° C. (850° F.); a pressure of between about 100 kPa (0 psig) and 7,000 kPa (1000 psig), preferably between about 275 kPa (25 psig) and 1400 kPa (200 psig); and a WHSV of between about 0.5 and 100, preferably between about 1.0 and 10.

Feedstocks to be utilized in the novel process of this invention can be generally described as hydrocarbons or oxygenated hydrocarbons. The particlar feedstock to be utilized will depend on the desired selective reaction. Thus, for example, in the disproportionation of toluene reaction in the selective production of para-xylene, in the ethylation of aromatics and in the selective production of para dialkyl substituted benzenes the feedstock would be aromatic and more particularly a mono-alkyl-substituted benzene feedstock, e.g., toluene. In converting alcohols and/or ethers to gasoline range product, the feedstock would comprise oxygenated hydrocarbons.

The following examples serve to illustrate the invention without limiting same.

EXAMPLE 1

Four grams of 1/16 inch extrudate containing 65% HZSM-5 were contacted with toluene, ethylene and hydrogen under reaction conditions of 100 psig, 380° C., WHSV (toluene) 28, and mole ratios of 7:1:3, respectively. The product ethyltoluenes contained 3.3% ortho-isomer. Ethylene was then switched out and 0.08 grams of 2,4,6-collidine were injected into the reactor in the toluene feed. When the ethylene flow was restored, the ethyltoluenes contained 41% para-isomer and less than 0.2% ortho isomer, with little change in toluene conversion.

In processes for the production of vinyl toluenes, a key economic factor is the production of low ortho isomer, since that isomer is untolerable in the ethyltoluene dehydrogenation step. The present example demonstrates a simple technique for producing ethyltoluenes very low in ortho-isomer.

EXAMPLE 2

The alkylation of toluene with ethylene was conducted in the vapor phase at 410° C. (770° F.) and a pressure of 790 kPa (100 psig) over an HZSM-5 catalyst. The catalyst was 1/16" extrudate containing 65% HZSM-5 (average crystal diameter 2 microns) in an alumina matrix and had been steamed 5 hours at 540° C. (1000° F.) prior to use. Toluene, ethylene and hydrogen were fed in a molar ratio of 10:1:4, respectively, at a WHSV (toluene)=30. Under these conditions, with this catalyst, the product ethyltoluenes contained about 54% para- and 0.3% ortho-isomer.

A slug of o-phenanthroline corresponding to 0.12 moles per mole of aluminum in the ZSM-5 was fed with the toluene (130 ppm N) for 15 minutes. At the end of this treatment the product ethyltoluenes (ET) contained 95.7% (PET) para- and <0.05% ortho-isomer (OET). Toluene conversion was 92% of theoretical, based on the ethylene:toluene mole ratio.

Following the slug, o-phenanthroline was fed at a constant rate in the toluene stream (30 ppm N). After 3.25 hours on stream, the product ethyltoluenes contained 96.8% para-isomer and undectectable ortho-isomer. Toluene conversion was 93% of theoretical.

The o-phenanthroline in the toluene was then reduced to 10 ppm nitrogen. After an additional 1.5 hours, the product ethyltoluenes contained 95.8% para-isomer and no detectable ortho-isomer. Toluene conversion was 89% of theoretical.

Pure toluene was then fed to the unit. After an additional 1.5 hours, the product ethyltoluenes contained 92.2% para-isomer and no detectable ortho-isomer. Toluene conversion was 89% of theoretical.

EXAMPLE 3

The procedures of Example 2 were repeated except that the initial slug corresponded to 0.25 moles of 8-phenanthroline per mole of aluminum in the ZSM-5 (a 30 minute treatment). Following the slug, the ethyltoluenes contained 96.8% para and no detectable ortho-isomer. Toluene conversion was 91% of theoretical.

The heterocycle was then fed at a steady 30 ppm N in the toluene. After 3.5 hours on stream, the ethyltoluene was 97.3% para, no ortho; toluene conversion was 92% of theoretical.

The heterocycle level was then reduced to 10 ppm nitrogen after 5.2 hours on stream with analysis showing 96.5% PET/ET, O OET/ET, 89% theoretical toluene conversion.

Pure toluene was then fed for 1 hour. The product was analyzed to be 95.6% PET/ET, O OET/ET, and 90% theoretical toluene conversion. Ethylene and toluene selectivities to ethyltoluenes were both 94%.

EXAMPLE 4

The procedures of Example 2 were repeated except that o-phenanthroline was fed constantly with the toluene at a level of 130 ppm N. The 130 ppm N is equivalent to 0.5 moles of heterocycle per aluminum in the zeolite per hour (0.5 H/Al hr.). After 1.75 hours on stream the ethyltoluenes contained 96.9% PET and no detectable OET. Toluene conversion was 91% of theory. After 3.25 hours on stream the corresponding results were 98.2% PET, O OET, and 90% conversion.

The feed was switched to pure toluene at this point. After 5.25 hours on stream, the product analysis was 94.2% PET/Et, O OET/Et, and 87% conversion.

EXAMPLE 5

The procedures of Example 4 were repeated except that the heterocycle was 2,4,6-collidine, fed at a constant 135 ppm N (1 H/Al hr.). The ethyltoluene product selectivity lined out at 61% para with no detectable ortho-isomer.

EXAMPLE 6

The procedures of Example 5 were repeated except that the collidine was present at 2800 ppm (25 H/Al hr.). The ethyltoluene selectivity exceeded 99% para with no ortho-isomer.

EXAMPLE 7

The procedure of Example 4 were repeated except that the heterocycle was 4-methylquinoline, fed at a constant 135 ppm N. Ethyltoluene selectivity lined out at 93-94% para with no detectable ortho-isomer.

EXAMPLE 8

The procedures of Example 4 were repeated except that the heterocycle was 2,6-lutidine, fed at a constant rate of 130 ppm N (1 H/Al hr.). After one hour of contact with the heterocycle, the catalyst was effectively dead.

EXAMPLE 9

The procedures of Example 3 were repeated except that the heterocycle was 4,7-diphenyl-1,10-phenanthroline. Following the slug, the feed toluene contained 10 ppm N. After 3.25 hours on stream, the ethyltoluenes were 66% PET with no detectable OET.

EXAMPLE 10

The procedures of Example 3 were repeated except that the catalyst contained ZSM-5 of a smaller crystal size (about 0.6 microns), steamed 6 hours at 540° C. Following the slug, o-phenanthroline was fed at 30 ppm N in the toluene. After 2.75 hours on stream, the ethyltoluenes contained 90.6% PET with no detectable OET.

EXAMPLE 11

The procedure of Example 4 were repeated except that phenanthrene was used in place of the heterocycle (at the same molar concentration in the toluene). The initial ethyltoluene product (before introduction of phenanthrene) was 54.2% para and 0.38% ortho isomer; after 1.25 hours on stream: 53.7% PET/ET and 0.28% OET/ET; and after 4.5 hours on stream: 53.9% PET/ET and 0.26% OET/ET. Toluene conversion (theoretical) decreased from 99 to 94 to 94%, respectively.

EXAMPLE 12

The procedures of Example 4 were repeated with 7,8-benzoquinoline, fed at a constant level of 130 ppm N. Ethyltoluenes, after 3.75 hours on stream were 80% PET, and O OET. Toluene conversion was 93% of theory.

EXAMPLE 13

The procedures of Example 12 were repeated but with 5,6-benzoquinoline (130 ppm N). Ethyltoluenes at 3.75 hours on stream, were 86% PET and no OET. Toluene conversion was 97% of theory.

EXAMPLE 14

The procedure of Example 13 were repeated but at a lower level of 5,6-benzoquinoline (30 ppm N). After 3.75 hours on stream, ethyltoluenes were 79% PET and 0% OET. Toluene conversion ws 97% of theory.

EXAMPLE 15

The procedure of Example 2 were repeated but only an initial slug of heterocycle was used. Injection of 4-methylquinoline into the toluene in an amount corresponding to only 10% (mole) of the aluminum in the ZSM-5 changed the ethyltoluene product from 55% PET, 0.38% OET to 75% PET, no OET (1.5 hours after the slug).

EXAMPLE 16

The procedures of Example 15 were repeated except that unsteamed catalyst was used. The ethyltoluene product (1.5 hours after the slug) analyzed 87% PET, no OET.

EXAMPLE 17

The procedures of Example 15 were repeated except that the slug was o-phenanthroline, corresponding to 0.25 moles per mole of aluminum in the ZSM-5 and the temperature of the run was 420° C. The catalyst contained 7% Mg and 3% P. The initial ethyltoluene product (before the slug) analyzed 94.0% PET, 0.0% OET. The slug increased para-selectivity to 98.0%.

EXAMPLE 18

This example shows that beneficial effects can be achieved in other aromatics reactions such as toluene disproportionation. Reaction conditions were 495° C., 2870 kPa (400 psig), $H_2/HC=4$, WHSV=6.5, with a toluene feed containing 130 ppm N as o-phenanthroline. The initial xylene product was 28.3% para and 38.6% ortho isomer. After phenanthroline corresponding to 0.75 moles per mole of aluminum in the ZSM-5 had been fed, the xylenes contained 36.2% para and 18.3% ortho-isomer.

EXAMPLE 19

The procedures of Example 12 were repeated except that the catalyst was not subjected to steam prior to testing. After 3.75 hours on stream the ethyltoluenes analyzed 92.4% para and no detectable ortho-isomer. Toluene conversion was 37% of theory.

What is claimed is:

1. A process for conducting selective reactions of hydrocarbons and/or oxygenated hydrocarbons feeds which comprises conducting said selective reactions under conversion conditions in the presence of a catalyst comprising one or more zeolites having a silica to alumina mole ratio of at least 12 and a constraint index of 1 to 12 said catalyst being in contact with one or more bulky heterocyclic organic nitrogen compounds having an effective critical dimension of greater than 6.8 Angstroms and having a pKa of between about 3 and 9.

2. The process of claim 1 wherein said zeolite is selected from the group consisting of ZSM-5, ZSM-11, ZSM-12, ZSM-23, ZSM-35, ZSM-38 and ZSM-48.

3. The process of claim 2 wherein said zeolite is ZSM-5.

4. The process of claim 1 wherein the amount of nitrogen as nitrogen compound is present in amount corresponding to between about 5 ppm and 15% based on total feed.

5. The process of claim 4 wherein said amount of nitrogen as nitrogen compound is between about 10 ppm and 5000 ppm based on total feed.

6. The process of claim 1 wherein said nitrogen compound is continuously contacted with said catalyst.

7. The process of claim 1 wherein said nitrogen compound is intermittently contacted with said catalyst.

8. The process of claim 1 wherein said nitrogen compound serves as a solvent for the reaction.

9. The process of claim 1 wherein said nitrogen compound serves as a heat transfer medium for the reaction.

10. The process of claim 8 or 9 wherein said nitrogen compound represents between about 10% and 90% of the feed.

11. The process of claim 1 wherein said nitrogen compound is added to said reaction as an initial slug.

12. The process of claim 1 wherein said nitrogen compound is selected from the group consisting of aryl substituted heterocyclic compounds and alkyl substituted heterocyclic compounds.

13. The process of claim 12 wherein said aryl substituted heterocyclic compounds are phenyl substituted heterocyclic compounds.

14. The process of claim 12 wherein said alkyl substituted heterocyclic compounds are methyl substituted heterocyclic compounds.

15. The process of claim 1 wherein said nitrogen compound is selected from the group consisting of alkylated pyridine derivatives, quinoline, alkylated quinolines, three-ring heterocycles and derivatives of three-ring heterocycles.

16. The process of claim 15 wherein said alkylated pyridine derivatives are selected from the group consisting of collidine, 3,4-lutidine and pentamethylpyridine.

17. The process of claim 15 wherein said alkylated quinolines are selected from the group consisting of 4-methylquinoline, 2,4-dimethylquinoline, 4,8-dimethylquinoline, and 2,4,8-trimethylquinoline.

18. The process of claim 15 wherein said three-ring heterocycles are selected from the group consisting of benzoquinolines and phenanthrolines.

19. The process of claim 15 wherein said derivatives of three-ring heterocycles are selected from the group consisting of neocuproine and bathophenanthroline.

20. The process of claim 1 wherein said effective critical dimension is greater than 7.0 Angstroms.

21. The process of claim 1 wherein said catalyst prior to contact with said nitrogen compound and prior to contact with the feed is steamed at conditions including a temperature of between about 610° F. and 1200° F., a pressure of between about 0.2 psia and 35 psia and a contact time of between about 30 minutes and 24 hours.

22. The process of claim 21 wherein said conditions include a temperature of between about 750° F. and 1020° F., a pressure of between about 7 psia and 22 psia and a contact time of between about 1 hour and 10 hours.

23. The process of claim 1 wherein said selective reaction is the alkylation of aromatics and said conversion conditions include a temperature of between about 105° F. and 1110° F., a pressure of between about 0 psig and 1000 psig, a WHSV of between about 0.1 and 200 and a mole ratio of alkylation agent to aromatic compound of between about 0.05 and 20.

24. The process of claim 23 wherein said conversion conditions include a temperature of between about 390° F. and 840° F., a pressure of between about 25 psig and 500 psig, a WHSV of between about 1 and 50 and a mole ratio of alkylation agent to aromatic compound of between about 0.10 and 5.

25. The process of claim 23 wherein said alkylation is the production of dialkyl substituted benzene compounds low in the ortho-isomer.

26. The process of claim 23 wherein said alkylation is the selective production of predominantly para dialkyl substituted benzene compounds.

27. The process of claims 25 or 26 wherein said alkylation involves the reaction of toluene and ethylene.

28. The process of claim 24 wherein said alkylation is the selective production of para-xylene by the methylation of toluene.

29. The process of claim 1 wherein said selective reaction is the disproportionation of toluene and said conversion conditions include a temperature of between about 390° F. and 1110° F., a pressure of between about 0 psig and 1000 psig, and a WHSV of between about 0.1 and 20.

30. The process of claim 29 wherein said conversion conditions include a temperature of between about 800° F. and 1020° F., a pressure of between about 25 psig and 500 psig, and a WHSV of between about 0.5 and 5.

31. The process of claim 1 wherein said selective reaction is the xylene isomerization and said conversion conditions include a temperature of between about 500° F. and 1000° F., a pressure of between about 25 psig and 1000 psig, a WHSV of between about 1 and 50.

32. The process of claim 31 wherein said conversion conditions include a temperature of between about 600° F. and 900° F., a pressure of between about 25 psig and 400 psig, and a WHSV of between about 5 and 15.

33. The process of claim 31 wherein said conversion conditions further comprise a hydrogen/hydrocarbon mole ratio of between about 1 and 20.

34. The process of claim 33 wherein said hydrogen/hydrocarbon mole ratio is between about 2 and 8.

35. The process of claim 1 wherein said selective reaction is the conversion of alcohols and/or ethers to valuable hydrocarbons and said conversion conditions include a temperature of between about 500° F. and 1000° F., a pressure of between about 0 psig and 1000 psig, and a WHSV of between about 0.5 and 100.

36. The process of claim 35 wherein said conversion conditions include a temperature of between about 600° F. and 850° F., a pressure of between about 25 psig and 200 psig, and a WHSV of between about 1.0 and 10.

* * * * *

UNITED STATES PATENT AND TRADEMARK OFFICE
CERTIFICATE OF CORRECTION

PATENT NO. : 4,300,011
DATED : November 10, 1981
INVENTOR(S) : Louis D. Rollmann It is certified that error appears in the above-identified patent and that said Letters Patent are hereby corrected as shown below:

Column 4, line 1         "550°F" should be --555°F--

Column 13, line 18       "8-phenanthroline" should be
                         --o-phenanthroline--

Signed and Sealed this

Thirteenth Day of April 1982

|SEAL|

Attest:

GERALD J. MOSSINGHOFF

Attesting Officer        Commissioner of Patents and Trademarks